United States Patent [19]

Peyman

[11] Patent Number: 4,685,921

[45] Date of Patent: Aug. 11, 1987

[54] VARIABLE REFRACTIVE POWER, EXPANDABLE INTRAOCULAR LENSES

[76] Inventor: Gholam A. Peyman, 535 N. Michigan Ave., Apt. 3001, Chicago, Ill. 60611

[21] Appl. No.: 832,335

[22] Filed: Feb. 24, 1986

[51] Int. Cl.⁴ .................................................. A61F 2/16
[52] U.S. Cl. .................................................... 623/6
[58] Field of Search .......................................... 623/6

[56] References Cited

U.S. PATENT DOCUMENTS

| | | | |
|---|---|---|---|
| 4,253,199 | 3/1981 | Banko | 623/6 |
| 4,373,218 | 2/1983 | Schachar | 623/6 |
| 4,542,542 | 7/1983 | Wright | 623/6 |
| 4,573,998 | 3/1986 | Mazzocco | 623/6 |
| 4,585,457 | 4/1986 | Kalb | 623/6 |

*Primary Examiner*—Ronald L. Frinks
*Attorney, Agent, or Firm*—Thomas A. Kmiotek

[57] ABSTRACT

Disclosed are intraocular lenses which have an expandable or fillable bag means comprising the central lenticular portion of the lens and lenses which are expandable by filling chambers within a flexible central lenticular portion. The central lenticular portion additionally can comprise a solid lens portion. The expandable bag means or chambers are filled correlating to a desired refractive power after placement in the eye. The intraocular lenses can be inserted in the eye through relatively small incisions (less than about 4 mm). Subsequent changes in refractive power can be accomplished without removing the implanted intraocular lens and with minimal or no trauma. The intraocular lenses can be implanted in either the posterior chamber or capsular bag.

25 Claims, 16 Drawing Figures

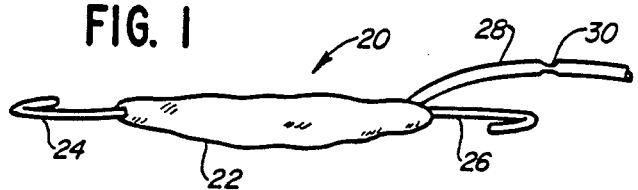
FIG. 1
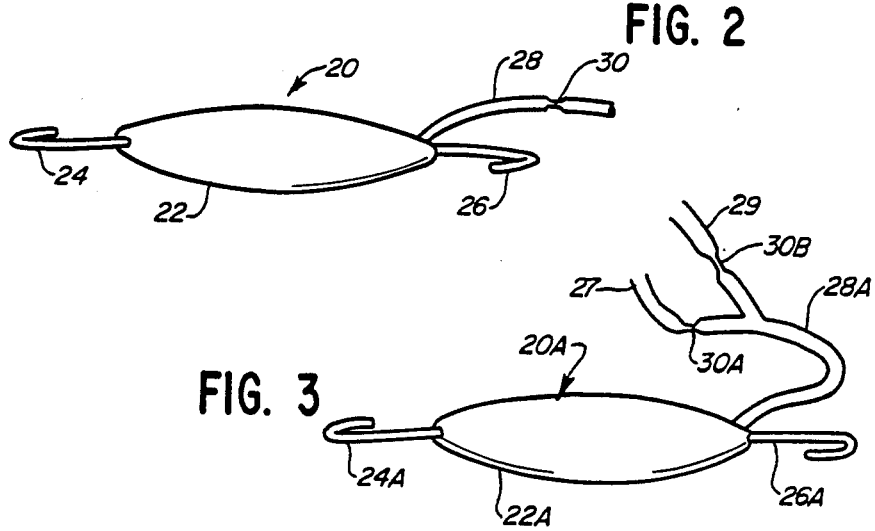
FIG. 2
FIG. 3
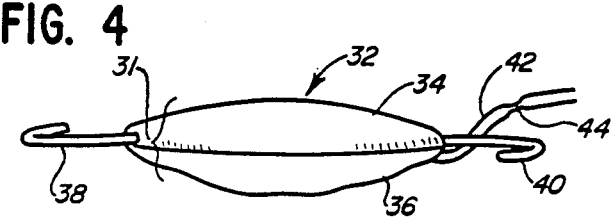
FIG. 4
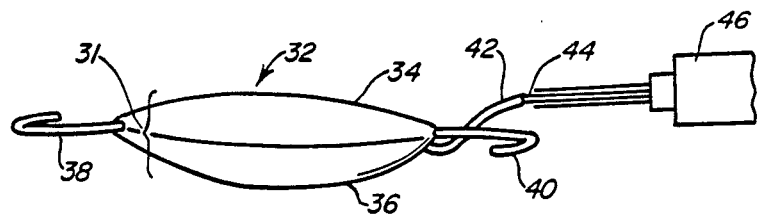
FIG. 5

FIG. 13
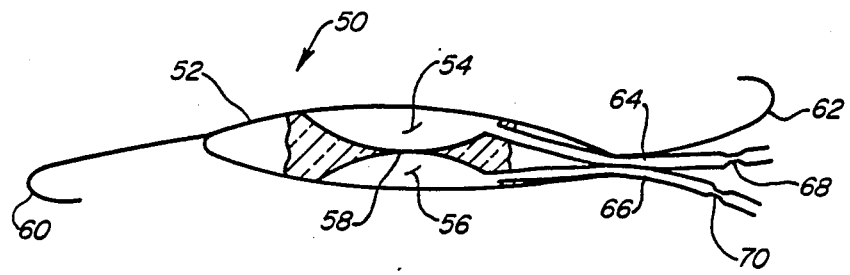
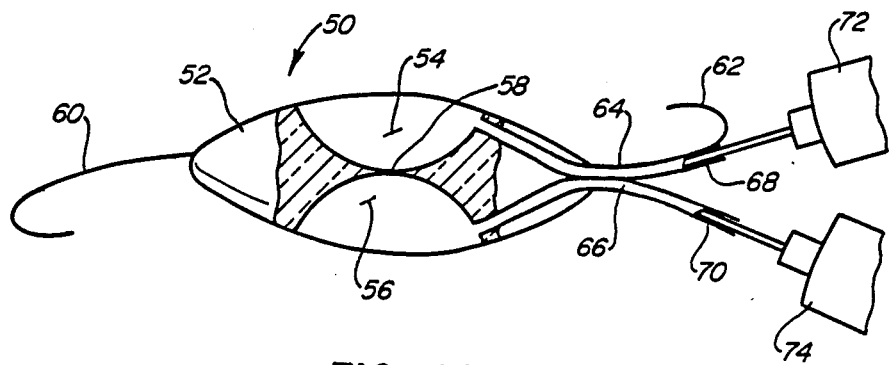
FIG. 14

FIG. 15
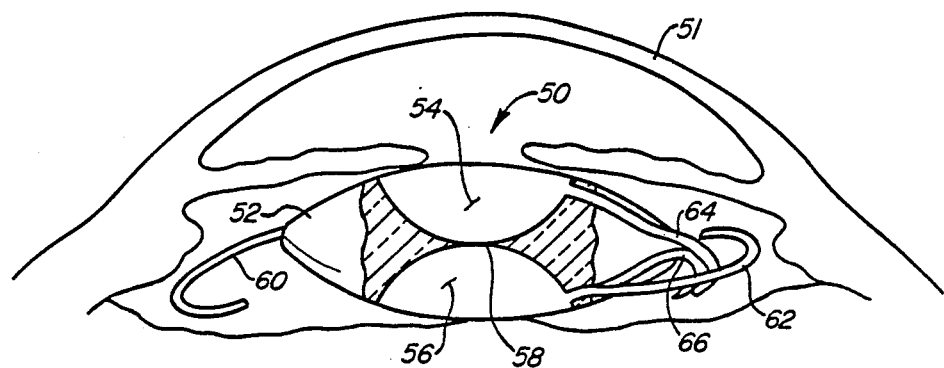
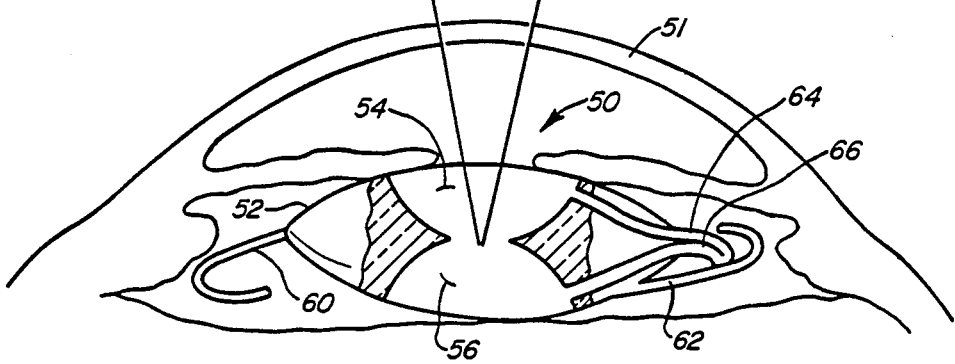
FIG. 16

VARIABLE REFRACTIVE POWER, EXPANDABLE INTRAOCULAR LENSES

FIELD OF THE INVENTION

Intraocular lenses for implanting inside aphakic eyes are the general province of this invention. This invention specifically relates to intraocular lenses whose central lenticular means initially is collapsed or unexpanded during insertion and implantation in the eye. This design obviates the need for a relatively large incision (greater than 4 mm) in the eye. The lens can be inserted through a relatively small incision (4 mm or less) in the eye.

The intraocular lenses of this invention can be implanted either in the posterior chamber or in the capsular bag. After placement in the eye, the bag means or chambers of the central lenticular means can be expanded by filling with the proper amount of a physiologically compatible fluid calculated to result in the correct refractive power for the patient. Moreover, after implantation if it becomes necessary to remove the lenses or to change their refractive power, only a small surgical incision is necessary.

For complete removal of the implanted lens, a syringe and needle can be used to extract the fluid and collapse the bag means by either puncturing the bag means or by accessing the tube means initially used to fill the bag means or chambers. Removal then can be accomplished through a similarly, relatively small (4 mm or less) incision. If only the refractive power of the implanted lenses need be changed, a syringe and needle can be used to add or remove physiologically compatible fluid by accessing through the tube means.

BACKGROUND OF THE INVENTION

Currently cataract extraction is the most common ophthalmic surgical procedure performed in the United States. Roughly, over 450,000 lenses are removed every year. These natural lenses, however, must be replaced with a prosthetic optical device before useful vision can be restored to the operated eye. Light rays no longer are focused on the retina with the lens removed. Vision is very poor without corrective glasses, contact lenses or an intraocular lens.

Corrective eye glasses have been the classic and most common method of correcting aphakia. Corrective glasses, however, being located in front of the normal position of the human lens, can produce magnification which distorts the shape of viewed objects. Contact lenses cause less magnification and distortion, but very old and very young patients frequently find handling and wearing these small lenses difficult. With implanted intraocular lenses, there is little or no magnification or distortion. Also, there is no need to remove the intraocular lens from the eye or otherwise handle the lens. Generally, intraocular lenses provide good visual acuity at all times, even at night.

Intraocular lenses have definite advantages in terms of vision and convenience over the other methods of aphakic correction. While intraocular lenses have definite advantages over corrective glasses and contact lenses, intraocular lenses have specific disadvantages.

Intraocular lens implantation surgery is more traumatic than simple cataract extraction alone. The additional handling of the cornea and manipulation inside the anterior chamber during lens implantation add to the amount of trauma to the eye. Extreme care must be exercised to limit trauma to the cornea, structures of the anterior chamber, and other structures.

Generally, during implant surgery, a 7–8 mm incision is made in the conjunctiva just outside the cornea so that the patient's lens can be removed and replaced with an implant intraocular lens. Incision length is dictated more by the size of the intraocular lens to be implanted than by the requirement of removing the patient's natural lens. For example, the patient's natural lens can be removed using an ultrasonic instrument which requires an incision much smaller than is needed to insert intraocular lens implants currently available.

The ability to change refractive power of an implanted intraocular lens without an additional surgical implant operation is a desired benefit. It is particularly desirable in very young patients. Size and shape of the eyeball in very young patients change as they mature. The distance from the lens to the retina changes as the size of the eye changes. A lens of the correct refractive power when implanted may not later correctly focus light entering the eye and passing to the retina. Changes in the refractive power of lenses in very young patients may be indicated after as little time as one year. It is the antithesis of limiting trauma associated with lens implants when a surgical procedure is dictated within such a short period of time.

A large number of different types and styles of intraocular lenses has been developed. Major classes of lenses can be distinguished based on the method of fixation in the eye. Anterior chamber lenses lie entirely in front of the iris. Iris-supported lenses rely on the structural integrity of the iris to stabilize and support the lens within the eye. Capsule-fixated lenses are inserted into a planned extracapsular cataract extraction space between the iris and posterior leaves of the lens capsule. Common to most lenses in use today are their reliance on haptics, also called feet or loops, emanating from the lenses and intended to support and fix the lens in the eye.

Trauma to the eye associated with lens implants is related to incision length. Efforts to minimize overall intraocular lens size, and hence reduce trauma, have so far concentrated on collapsing or folding haptic loops prior to insertion. Substantive efforts in this regard, along with attempts of others, may be found in U.S. patent applications Ser. Nos. 490,858, *Intraocular Lenses with Openable Haptic Loops*, filed May 2, 1983, and 800,728, *Intraocular Lenses with Latchable Haptic Loops*, filed Nov. 22, 1985 both to Peyman, commonly owned with this application by Gholam A. Peyman, M.D.

That the lenses always have to be larger than the incision provided for their implant in the eye is a principal cause of trauma. Implantation of currently used lenses in their proper position within the eye often requires the reduction of lens size inside the eye during surgery. In this microfine surgery uncommon agility on the part of even a skilled surgeon often is required. Space limitations in the eye, the required size of the lens once implanted, and considerable manipulations of the lenses during implantation by the surgeon can result in traumatic damage to the corneal endothelium and very often rupture of the posterior capsule by the novice. Damage to the corneal endothelium and rupture of the posterior capsule are complications considered serious.

Some attempts have been made to reduce the size of the central lenticular portion of intraocular lenses prior to insertion. Silicon lenses which can be folded and gel-type lenses which absorb intraocular fluid and subsequently expand do address the surgical trauma problem. Nevertheless, the incision required for these lenses, although less than the 7-8 mm length for solid intraocular lenses, is relatively large—about 4 mm in length.

A major concern of ophthalmic surgeons is choosing the correct refractive power for lenses. Patients risk additional surgery for lens removal and replacement if the choice of lens refractive power is too much in error. A risk commonly shared in the use of solid, silicon, and gel-type lenses is additional surgery since it is the only alternative for changing a refractive power too much in error.

It would be expedient to offer an intraocular lens that could be implanted in a very nearly atraumatic manner.

It would be desirable if an intraocular lens were provided that during surgical implantation was small for easy insertion into the eye with minimum trauma to the cornea and other structures while later being easily made larger to effect a firm, secure fit in the eye.

It also would be desirable to offer an intraocular lens that could be inserted into the eye through a relatively small incision (4 mm or less) such that the lenses can be implanted by relatively inexperienced implant surgeons without considerable manipulations of the lens during surgery. Damage to the corneal endothelium and rupture of the posterior capsule would occur less often, thus minimizing compromises to a patient's welfare.

It also would be expedient to offer an intraocular lens where the refractive power could be precisely set once implanted while also offering the benefit of changing the refractive power subsequently with no or minimum invasion.

BRIEF DESCRIPTION OF THE INVENTION

The intraocular lens of this invention is designed for insertion into the posterior chamber or in the capsular bag of the eye of a mammal. A central lens portion, also referred to as central lenticular means, refracts light that will enter the eye through the cornea before the light passes to the retina. The central lenticular means preferably is made from a flexible, impermeable, physiologically compatible material that forms a bag means initially collapsed upon itself.

Alternatively, the central lenticular means is comprised of an anterior, solid lens portion and a posterior, flexible, impermeable bag means initially collapsed and made from a physiologically compatible material. One face of the solid lens portion can be open to the inside of the bag means or the bag means can be comprised entirely by the flexible, impermeable, physiologically compatible material and fixed to the solid lens portion. The solid lens portion preferably is made from silicon. Conversely, the central lenticular means also may be comprised of a posterior, solid lens portion and an anterior, flexible, impermeable bag means portion initially collapsed. The bag means can be comprised entirely of the flexible, impermeable, physiologically compatible material and fixed to the solid lens portion or the inside of the bag means can be open to one face of the solid lens portion.

In still another embodiment, the central lenticular means is comprised of a flexible, impermeable material such as silicon. The central lenticular means has at least two chambers therein which are separated by a relatively thin membrane.

Tube means open into the inside of the bag means or the chambers of the central lenticular means and extend outwardly therefrom. The bag means then can be expanded once the intraocular lens has been implanted by filling with a fluid passing through the tube means and entering the inside of the bag means. Similarly, the chambers can be filled with a fluid passing through the tube means and entering the chambers thereby expanding the central lenticular means. Once the bag means or the chambers have been filled, the tube means can be severed and sealed to prevent fluid escape. Alternatively, valve means—such as a sphincter—can comprise a portion of the tube means thus allowing subsequent changes in fluid volume in the bag means or the chambers.

The central lenticular means can be biconvex, convex-plain, or convex-concave. Haptic means, feet or loops are attached to the central lenticular portion and function to hold the lens in place in the eye. Haptic means commonly are made from polypropylene or other synthetic polymers. Generally, the lenses have at least two haptic means, but intraocular lenses with more than two haptic means are not uncommon. First ends of the haptic means are fixed to the central lenticular means.

Reducing the size of the entire intraocular lens structure in the manner of this invention permits generally atraumatic insertion of the lens into the eye obviating extreme surgical manipulations and contortions of the lens within the eye. Once the lens of this invention is inserted into its desired position within the eye, the refractive power of the lens can be set by adding fluid to the bag means or chambers through the tube means. The amount of fluid added to the bag means or chambers using a calibrated needle/syringe combination can be measured precisely and the refractive power chosen by equating fluid volume with refractive power. The entire procedure of implant and filling can be accomplished through a relatively small incision of less than approximately 4 mm—a considerably smaller incision than the 7-8 mm incision made so that conventional, hard lenses can be inserted. The tube means accessing the chambers or the inside of the bag means then is sealed when the correct refractive power is reached.

Alternatively, valve means—such as a sphincter valve—seal the tube means once the desired amount of fluid fills the chambers or the bag means. Valve means in the tube offer considerably more flexibility in treating patients as well. Very young patients would benefit considerably from such a structure. As eye shape and size change when very young patients mature, a refractive power correctly chosen during surgery may become incorrect as the distance from the lens to the retina changes. Light no longer is focused on the retina and visual acuity suffers. Eye glasses or contact lenses have been employed to correct a patient's vision in such instances. Otherwise, patients must undergo additional, conventional surgery to remove and replace the implanted lenses.

With this invention, however, subsequent surgical procedures would be less invasive since replacement of the lenses is not indicated. A relatively small incision of 4 mm or less provides access to the tube means. Fluid thus can be added or removed as necessary from the bag means or the chambers of the intraocular lenses to change the refractive power of the previously implanted lenses.

Alternative embodiments of this invention also obviate the need to remove a previously implanted lens. Lenses comprised of either an anterior or posterior solid lens portion and a corresponding posterior or anterior flexible, impermeable bag means portion previously filled with fluid to the desired volume for the refractive power indicated during implant need not be removed to change the refractive power. Fluid in the bag means can be added or removed as described above to reset the refractive power of the lens. More significant, though, is that surgical intervention via incision can be eliminated altogether. Using a Yttrium-Aluminum Garnet (YAG) laser, the flexible, impermeable bag means can be ruptured, vaporized or both. A physiological compatible fluid (polyvinyl alcohol for example) chosen to be absorbable by the body and filling the bag means would escape to be absorbed. The solid lens portion of the central lenticular means would remain as the implanted lens.

Lenses comprised of a central lenticular means made from a flexible, impermeable material and having at least two chambers therein analogously can have their refractive power changed. Fluid in the chambers can be added or removed to change the shape of the central lenticular means thereby resetting the refractive power of the lens.

In this embodiment surgical intervention via incision also can be eliminated. A YAG laser can be used to rupture and vaporize the membrane separating the two chambers. Eliminating refractive surfaces in this manner changes the refractive power of the lens.

In any embodiment, if the surgeon is confident about the precise refractive power needed in the eye, the bag means or chambers can be filled with self-polymerizing, physiologically compatible monomers or a combination of monomers and fixing agents. With the latter choice of monomer and fixing agent, a double-barrelled tube means or separate tube means converging to a single tube means accessing the bag means is used. This embodiment also has the advantage that the lens still is inserted via a relatively small incision. Filling the bag means or chambers still is accomplished after the lens is implanted.

A benefit of this invention resides in the ease of lens insertion through a relatively small surgical incision and minimal intraocular manipulation offered to the surgeon by the particular designs disclosed herein. The intraocular lens is compact in structure. Trauma associated with insertion and proper placement within the eye thereby is minimized.

Another benefit of this invention is that during insertion, the intraocular lens, and in particular the central lenticular means, is small for easy insertion into the eye with minimum trauma to the cornea and other structures while later being made easily larger to effect a firm, secure fit in the eye.

Another benefit of this invention is that it can be implanted by relatively inexperienced implant surgeons without manipulation of the lens during surgery.

Still another benefit of this invention is that the refractive power can be precisely set once implanted while also offering the benefit of changing the refractive power subsequently with no or minimum invasion.

Other benefits and advantages of this invention will become apparent upon reading the following detailed description and appended claims.

BRIEF DESCRIPTION OF THE DRAWINGS

For a more complete understanding of this invention, reference should now be had to the embodiments illustrated in greater detail in the accompanying drawings.

In the drawings:

FIG. 1 is a perspective view of one embodiment of the intraocular lens of the present invention showing the bag means in a deflated or unfilled state.

FIG. 2 is a perspective view of the intraocular lens of the present invention showing the bag means in an inflated or filled state.

FIG. 3 is a perspective view of another embodiment of the intraocular lens of the present invention showing the bag means in a deflated or unfilled state and showing two tube means converging to one tube means.

FIG. 4 is a perspective view of another embodiment of the intraocular lens of the present invention with a central lenticular means having a solid, anterior portion and a posterior, deflated or unfilled bag means.

FIG. 5 is a perspective view of the intraocular lens with a central lenticular means having a solid, anterior portion and inflated or filled posterior bag means.

FIG. 13 is a perspective view of another embodiment of the intraocular lens of the present invention showing a flexible, impermeable central lenticular means having two chambers therein.

FIG. 14 is a perspective view of the intraocular lens having a flexible, impermeable central lenticular means and showing its chambers filled with fluid.

FIG. 15 is a cut-away view of a mammalian eye showing the intraocular lens of the present invention implanted in the eye with the chambers filled with fluid.

FIG. 16 is a cut-away view of a mammalian eye showing the intraocular lens of the present invention implanted in the eye and with a flexible, impermeable central lenticular means having chambers filled with fluid and also showing a YAG laser disrupting the membrane separating the chambers.

DESCRIPTION OF THE PREFERRED EMBODIMENTS

Figure 6:
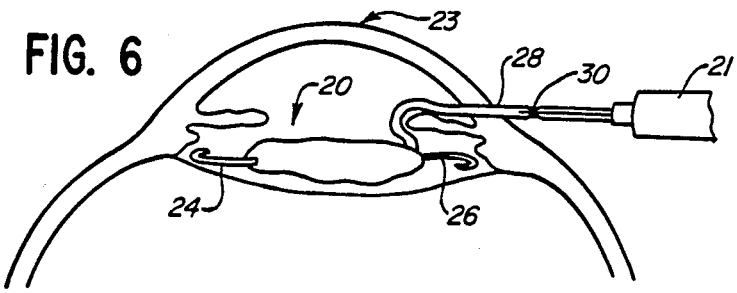
FIG. 6 is a cut-away view of a mammalian eye showing the intraocular lens of the present invention implanted in the eye and having a deflated or unfilled bag means.

One embodiment of the intraocular lens 20 of this invention is illustrated in FIG. 1. Intraocular lens 20 has central lenticular means 22 and haptic means 24 and 26. Preferably, central lenticular means 22 is made from a flexible, impermeable, physiologically compatible material conventionally available. Central lenticular means 22 also is referred to as bag means since central lenticular means 22 forms a bag having an inside and an outside. Resilient haptic means 24, 26 preferably are made from polypropylene, other polyolefin, polymethylmethacrylate, or the like. Resilient haptic means 24, 26 are fixedly attached to central lenticular means 22 and act to stabilize implanted intraocular lens 20. Tube means 28 is attached to, and opens into, the inside of bag means (central lenticular means) 22 and extends outwardly therefrom.

Bag means 22 in FIG. 1 is shown in its collapsed or unexpanded or unfilled or deflated condition. In its unfilled condition, bag means 22 is sufficiently small to enable intraocular lens 20 to be inserted into the eye of a mammal through a relatively small (less than 4 mm) incision subsequent to the removal of the eye's natural lens. Tube means 28 also may additionally comprise valve means 30 proximate bag means 22 which valve means 30 is open when fluid is passing through tube means 28 and which valve means 30 is closed when fluid is not passing through said tube means 28.

Once intraocular lens 20 has been implanted, bag means 22 is expanded by filling with a fluid passing through tube means 28 and entering the inside of bag means 22. The amount of fluid added to the inside of bag means 22, using for example a calibrated needle/syringe combination, can be measured precisely and the refractive power of bag means 20 (central lenticular means) chosen by equating fluid volume with refractive power. Fluid filling bag means 20 preferably is a physiologically compatible fluid such as silicones, gelatins, polyvinyl alcohols or the like. Alternatively, bag means 20 may be filled with a self-polymerizing, physiologically compatible monomer or a combination of monomer and fixing agent.

Tube means 28 is shown having valve means 30 which may be a sphincter valve. With this embodiment, tube means 28 having valve means 30 allows fluid to pass through tube means 28 under sufficient positive or negative external pressure. Valve means 30 remains closed under static pressure once bag means 22 has been filled with fluid. One advantage to this structure having tube means 28 with valve means 30 is that subsequent changes in refractive power to intraocular lens 20 can be accomplished without removing intraocular lens 20 for replacement. A relatively small incision (less than 4 mm) can be made to access tube means 28 with a needle/syringe to add or remove fluid thus minimizing trauma associated with more invasive techniques.

Alternatively, tube means 28 can be severed and sealed after the desired amount of fluid fills bag means 22 of intraocular lens 20. Only a small portion of tube means 28 remains in the eye after implantation. Fluid escape from bag means 22 through tube means 28 is prevented.

Filled bag means 22 of intraocular lens 20 is illustrated in FIG. 2. The shape of bag means 22, in its filled condition can be biconvex, convex-plain, or convex-concave.

Illustrated in FIG. 3 is intraocular lens 20A having central lenticular means/bag means 22A. Resilient haptic means 24A, 26A are fixedly attached to bag means 22A. Tube means 28A opens into the inside of central lenticular means/bag means 22A. Tube means 28A has branch tube means 27, 29 which converge to form tube means 28A. Branch tube means 27, 29 have valve means 30A, 30B which function to control fluid flow into and out of bag means 22A.

The embodiment of FIG. 3 typically would be used when fluid chosen to fill bag means 22A is a physiologically compatible monomer and its fixing agent. Monomer and fixing agent thus could be kept separate until just prior to entering bag means 22A through tube means 28A.

Tube means 28A can be severed and sealed once the desired amount of fluid fills bag means 22A of implanted intraocular lens 20A. Alternatively, tube means 28A can be left intact in the eye.

Figure 7:
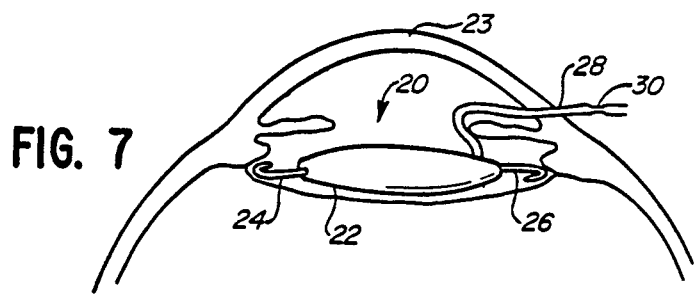
FIG. 7 is a cut-away view of a mammalian eye showing the intraocular lens of the present invention implanted in the eye and having an inflated or filled bag means.
Figure 8:
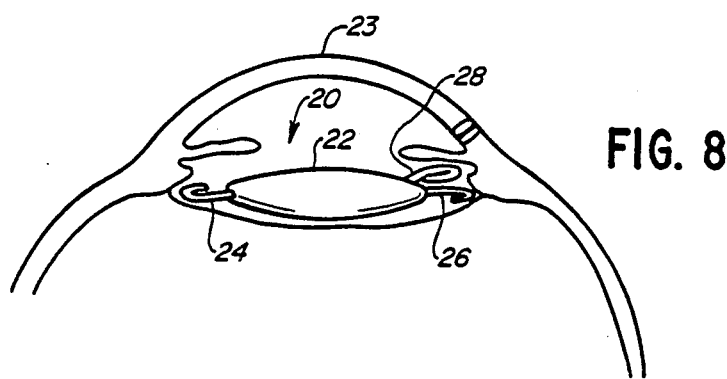
FIG. 8 is a cut-away view of a mammalian eye showing the intraocular lens of the present invention implanted in the eye and having an inflated or filled bag means and a sealed tube means and a closed incision in the eye.

FIGS. 6, 7 and 8 show the embodiment of intraocular lens 20 in FIGS. 1 and 2 implanted in the eye of a mammal. FIG. 6 illustrates intraocular lens 20 implanted in eye 23 with bag means 22 in its unfilled condition. Needle/syringe means 21 is used to fill bag means 22 with fluid via tube means 28. Filled bag means of intraocular lens 20 is shown in FIGS. 7 and 8. FIG. 7 shows tube means 28 having valve means 30 prior to placing tube means 28 in the eye. With valve means 30 intact, fluid subsequently can be added or removed from bag means 22. FIG. 8 demonstrates that tube means 28 can be severed and sealed before being placed in eye 23.

Figure 9:
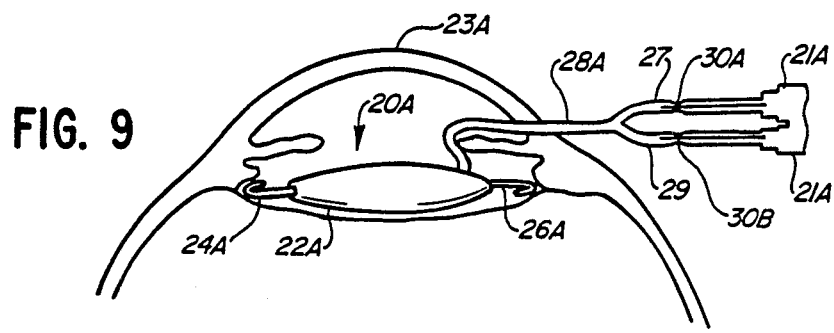
FIG. 9 is a cut-away view of a mammalian eye showing another embodiment of the intraocular lens of the present invention implanted in the eye and showing two tube means converging to one tube means.

FIG. 9 reveals intraocular lens 20A of FIG. 3 implanted in eye 23A. Needle/syringe means 21A fills tube means 28A with monomer and fixing agent entering tube means 28A through converging tube means 27, 29. Tube means 28A will be severed and sealed before being placed in eye 23A.

Another embodiment of this invention is illustrated in FIGS. 4 and 5. Intraocular lens 32 is shown having central lenticular means 31 comprised of a solid lens means 34 and a flexible, impermeable bag means 36 fixed to solid lens means 34. Bag means 36 either can be entirely closed or have its inside open to one face of solid lens means 34. Preferably, solid lens means 34 is made from silicon, but any material conventionally used is suitable. Bag means 36 preferably is made from a flexible, impermeable, physiologically compatible material conventionally available. Haptic means 38, 40 fixedly attached to central lenticular means 31—preferably attached to solid lens means 34—preferably are made from polypropylene, other polyolefin, polymethylmethacrylate or the like. Haptic means 38, 40 act to stabilize implanted intraocular lens 32.

It should be appreciated that, depending on placement in the eye, solid lens means 34 can comprise either the posterior or anterior portion of central lenticular means 31. Conversely, bag means 36 can comprise either the anterior or posterior portion of central lenticular means 31.

Tube means 42 are attached to open into the inside of bag means 36 and tube means 42 extends outwardly therefrom. Bag means 36 is shown in its collapsed or unfilled or deflated or unexpanded condition in FIG. 4. FIG. 5 shows bag means 36 in its filled or inflated condition. In its unfilled condition, bag means 36 effectively reduces the size of central lenticular means 31 minimizing the incision size necessary for implanting intraocular lens 32. Tube means 42 also may additionally comprise valve means 44—preferably sphincter valve means—proximate bag means 36. Valve means 44 is open when fluid is passing through tube means 42. Valve means 44 is closed when fluid is not passing through tube means 42.

Bag means 36 is expanded once intraocular lens 32 has been implanted by filling with a fluid passing through tube means 42 and entering the inside of bag means 36. The amount of fluid added to the inside of bag means 36, using a calibrated needle/syringe means 46, can be measured precisely and the refractive power of central lenticular means 31 chosen by equating fluid volume with refractive power. Fluid filling bag means 36 preferably is a physiologically compatible fluid such as silicones, gelatins, polyvinyl alcohols or the like.

Tube means 42, having valve means 44, allows fluid to pass through tube means 42 under sufficient positive or negative pressure, but valve means 44 remains closed under static pressure once bag means 36 has been filled with fluid. One advantage to the structure having tube means 42 with valve means 44 is that subsequent changes in refractive power to intraocular lens 32 can be accomplished without removing intraocular lens 32 for replacement. A relatively small incision (less than 4 mm) can be made in the eye for accessing tube means 42. Fluid then can be added or removed with minimal trauma.

Alternatively, tube means 42 can be severed and sealed after the desired amount of fluid fills bag means 36. Only a small portion of tube means 42 remains in the eye after implantation and fluid escape from bag means 36 through tube means 42 is prevented.

Figure 10:
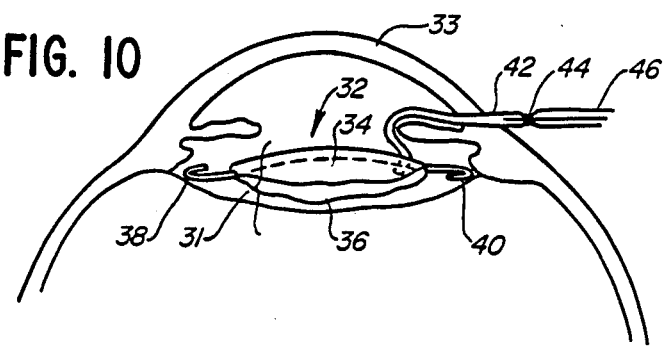
FIG. 10 is a cut-away view of a mammalian eye showing another embodiment of the intraocular lens of the present invention implanted in the eye and with a central lenticular means having a solid, anterior portion and a posterior, deflated or unfilled bag means.
Figure 11:
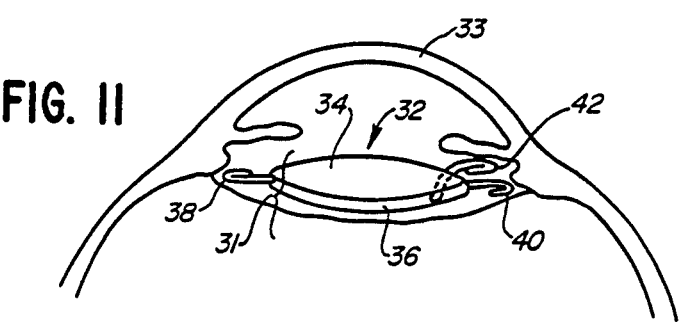
FIG. 11 is a cut-away view of a mammalian eye showing the intraocular lens of the present invention implanted in the eye and with a central lenticular means having a solid, anterior portion and a posterior, inflated or filled bag means.
Figure 12:
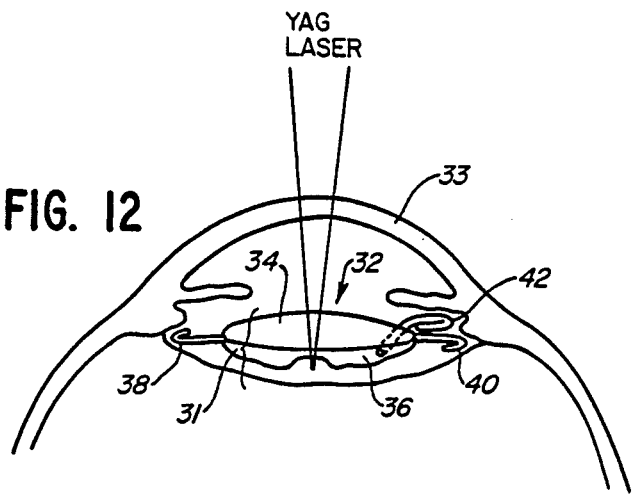
FIG. 12 is a cut-away view of a mammalian eye showing the intraocular lens of the present invention implanted in the eye and with a central lenticular means having a solid, anterior portion and a posterior, inflated or filled bag means and also showing a YAG laser disrupting the bag means.

FIGS. 10, 11 and 12 show the embodiment of intraocular lens 32 in FIGS. 4 and 5 implanted in the eye of a mammal. FIG. 10 illustrates intraocular lens implanted in eye 33 with bag means 36 in its unfilled or unexpanded condition. Needle/syringe means 46 is used to fill bag means 36 via tube means 42 with fluid. Filled bag means 36 of intraocular lens 32 is shown in FIGS. 11 and 12 both illustrating severed and sealed tube means 42 placed in eye 33.

Significantly, FIG. 12 illustrates that the refractive power of intraocular lens 32 can be changed subsequent to implantation, without removing the intraocular lens, and without surgical incision. Using a Yttrium-Aluminum Garnet (YAG) laser, flexible, impermeable bag means 36 can be ruptured, vaporized or both. A physiological compatible fluid (polyvinyl alcohol for example) chosen to be absorbable by the body fills bag means 36. This fluid escapes to be absorbed. Solid lens means 34 remains intact and unharmed. Intraocular lens 32 would have the refractive power of solid lens means 34.

Still another embodiment of this invention is illustrated in FIGS. 13, 14, 15 and 16. Intraocular lens 50 has central lenticular means 52 comprised of a flexible, impermeable material such as silicon and having two chamber means 54, 56 separated by membrane 58. Haptic means 60, 62 fixedly attached to central lenticular means 52 preferably are made from silicon, polypropylene, other polyolefin or the like. Haptic means 60, 62 act to stabilize implanted intraocular lens 50.

Tube means 64, 66 are attached to central lenticular means 52 and open into chamber means 54, 56, and tube means 64, 66 extend outwardly therefrom. FIG. 13 shows chamber means 54, 56 in their unfilled state and central lenticular means 52 in its unexpanded condition. In its unexpanded condition, central lenticular means 52 can be implanted through a relatively small incision. Tube means 64, 66 also may additionally comprise valve means 68, 70—preferably sphincter valve means—proximate central lenticular means 52. Valve means 68, 70 open when fluid is passing through tube means 64, 66. Valve means 68, 70 are closed when fluid is not passing through tube means 64, 66.

Chamber means 54, 56 are filled and central lenticular means 52 is expanded once intraocular lens 50 has been implanted. The amount of fluid added to chamber means 54, 56, using a calibrated needle/syringe means 72, 74 (FIG. 14) can be measured precisely and the refractive power of central lenticular means 52 chosen by equating fluid volume with refractive power. Fluid filling chamber means 54, 56 can be a gas or a physiologically compatible fluid such as silicones, gelatins, polyvinyl alcohols or the like.

Tube means 64, 66, having valve means 68, 70, allows fluid to pass through tube means 64, 66 under sufficient positive or negative pressure. Valve means 68, 70 remain closed under static pressure once chamber means 54, 56 have been filled with fluid. FIG. 14 shows chamber means 54, 56 filled with fluid and central lenticular means 52 in its expanded condition.

One advantage to the structure having tube means 64, 66 with valve means 68, 70 is that subsequent changes in refractive power to intraocular lens 52 can be accomplished without removing intraocular lens 52 for replacement. A relatively small incision (less than 4 mm) can be made in the eye for accessing tube means 64, 66. Fluid then can be added or removed with minimal trauma.

Alternatively, tube means 64, 66 can be severed and sealed after the desired amount of fluid fills chamber means 54, 56. Only a small portion of tube means 64, 66 remains in the eye after implantation. Fluid escape from chamber means 54, 56 thereby is prevented.

FIGS. 15 and 16 show the embodiment of introcular lens 50 implanted in the eye of a mammal. FIGS. 15 and 16 show filled chamber means 54, 56 and expanded central lenticular means 52 illustrating severed and sealed tube means 64, 66 placed in eye 51.

Significantly, FIG. 16 illustrates that the refractive power of intraocular lens 50 can be changed subsequent to implantation. This is accomplished without removing intraocular lens 50 and without surgical incision. Using a YAG laser, membrane 58 separating chamber means 54, 56 is ruptured and vaporized. Membrane 58 acting as a refractive surface disappears. Intraocular lens 50 would have a resulting refractive power determined by the remaining refractive surfaces of central lenticular means 52 and the fluid remaining in the new combined chamber means 54, 56.

It should be appreciated that the embodiments of this invention described above result in a compact intraocular lens structure which is easily implantable. Trauma generally associated with implantation of intraocular lenses can be reduced by use of this invention.

A singular benefit of the embodiments of this invention resides in that refractive power of the implanted lens can be changed subsequent to implantation, without removing the intraocular lens, and with minimal or no trauma. This benefit is particularly important to patients who are very young. Eye size change in very young patients as they mature thus necessitates a reduction in intraocular lens refractive power.

The above has been offered for illustrative purposes and is not intended to limit the invention of this application which is defined in the claims below.

I claim:

1. Intraocular lens for insertion inside the eye of a mammal comprising:

central lenticular means for refracting light entering the eye through the cornea before light passes to the retina, said central lentiular means comprised of a solid lens portion and a flexible, impermeable bag means portion connected thereto and collapsed upon itself and forming an inside and an outside; and, tube means opening into said inside of said bag means of said central lenticular means and extending outwardly therefrom wherein said bag means can be expanded once said intraocular lens has been inserted inside the eye of a mammal by filling with a fluid passing through said tube means and entering said inside of said bag means whereby said flexible, impermeable bag means being disruptable to change said lens' refractive power and said solid lens portion remaining intact and unharmed subsequent to disruption.

2. The intraocular lens of claim 1 wherein said solid lens portion is anterior said flexible, impermeable bag means portion.

3. The intraocular lens of claim 1 wherein said solid lens portion is posterior said flexible, impermeable bag means portion.

4. The intraocular lens of claim 1 wherein said tube means additionally comprises valve means proximate said bag means, said valve means being open when fluid is passing through said tube means and said valve means being closed when fluid is not passing through said tube means.

5. The intraocular lens of claim 2 wherein said tube means additionally comprises valve means proximate said bag means, said valve means being open when fluid is passing through said tube means and said valve means being closed when fluid is not passing through said tube means.

6. The intraocular lens of claim 1 wherein said tube means additionally comprises a sphincter valve proximate said bag means which sphincter valve opens upon sufficient external pressure of fluid passing through said tube means and which sphincter valve remains closed under static pressure from fluid inside of said bag means.

7. The intraocular lens of claim 2 wherein said tube means additionally comprises a sphincter valve proximate said bag means which sphincter valve opens upon sufficient external pressure of fluid passing through said tube means and which sphincter valve remains closed under static pressure from fluid inside of said bag means.

8. The intraocular lens of claim 1 wherein said fluid filling said flexible, impermeable bag means consists essentially of a material selected from the group consisting of physiological compatible monomers which polymerize to polymers, silicones, gelatins, and polyvinyl alcohols.

9. The intraocular lens of claim 2 wherein said fluid filling said flexible, impermeable bag means consists essentially of a material selected from the group consisting of physiological compatible monomers which polymerize to polymers, silicones, gelatins, and polyvinyl alcohols.

10. The intraocular lens of claim 1 additionally comprising at least two resilient haptic means for stabilizing and holding in place in the eye said central lenticular means.

11. The intraocular lens of claim 2 additionally comprising at least two resilient haptic means for stabilizing and holding in place in the eye said central lenticular means.

12. The intraocular lens of claim 3 additionally comprising at least two resilient haptic means for stabilizing and holding in place in the eye said central lenticular means.

13. The intraocular lens of claim 4 additionally comprising at least two resilient haptic means for stabilizing and holding in place in the eye said central lenticular means.

14. The intraocular lens of claim 5 additionally comprising at least two resilient haptic means for stabilizing and holding in place in the eye said central lenticular means.

15. The intraocular lens of claim 6 additionally comprising at least two resilient haptic means for stabilizing and holding in place in the eye said central lenticular means.

16. The intraocular lens of claim 7 additionally comprising at least two resilient haptic means for stabilizing and holding in place in the eye said central lenticular means.

17. The intraocular lens of claim 23 additionally comprising at least two resilient haptic means for stabilizing and holding in place in the eye said central lenticular means.

18. The intraocular lens of claim 9 additionally comprising at least two resilient haptic means for stabilizing and holding in place in the eye said central lenticular means.

19. The intraocular lens for insertion inside the eye of a mammal comprising:

central lenticular means for refracting light entering the eye through the cornea before light passes to the retina, said central lenticular means comprised of a flexible, impermeable material and having at least two chamber means therein separated by a membrane; and, tube means opening into each of said chambers of said central lenticular means and extending outwardly therefrom wherein said chambers are filled with a fluid passing through said tube means and entering said chambers once said intraocular lens has been inserted inside the eye thereby expanding said central lenticular means.

20. The intraocular lens of claim 19 wherein said tube means additionally comprise valve means proximate said central lenticular means, said valve means being open when fluid is passing through said tube means and said valve means being closed when fluid is not passing through said tube means.

21. The intraocular lens of claim 19 wherein said tube means additionally comprises a sphincter valve proximate said central lenticular means which sphincter valve opens upon sufficient external pressure of fluid passing through said tube means and which sphincter valve remains closed under static pressure from fluid inside said chamber means.

22. The intraocular lens of claim 19 additionally comprising at least two resilient haptic means for stabilizing and holding in place in the eye said central lenticular means.

23. The intraocular lens of claim 21 additionally comprising at least two resilient haptic means for stabilizing and holding in place in the eye said central lenticular means.

24. The intraocular lens of claim 22 wherein said fluid filling said chamber means consists essentially of a material selected from the group consisting of physiologically compatible gases, silicones, gelatins and polyvinyl alcohols.

25. The intraocular lens of claim 23 wherein said fluid filling said chamber means consists essentially of a material selected from the group consisting of physiologically compatible gases, silicones, gelatins and polyvinyl alcohols.

* * * * *